(12) United States Patent
Landskron et al.

(10) Patent No.: US 9,623,398 B2
(45) Date of Patent: Apr. 18, 2017

(54) ORGANONITRIDIC FRAMEWORKS WITH HIERARCHICAL PORE STRUCTURES AND HIGH GAS SELECTIVITY

(75) Inventors: Kai Landskron, Bethlehem, PA (US); Mohanty Paritosh, Saharanpur (IN)

(73) Assignee: Lehigh University, Bethlehem, PA (US)

( * ) Notice: Subject to any disclaimer, the term of this patent is extended or adjusted under 35 U.S.C. 154(b) by 764 days.

(21) Appl. No.: 13/640,161

(22) PCT Filed: Apr. 11, 2011

(86) PCT No.: PCT/US2011/031936
§ 371 (c)(1),
(2), (4) Date: May 31, 2013

(87) PCT Pub. No.: WO2011/127468
PCT Pub. Date: Oct. 13, 2011

(65) Prior Publication Data
US 2014/0087163 A1    Mar. 27, 2014

Related U.S. Application Data

(60) Provisional application No. 61/322,581, filed on Apr. 9, 2010, provisional application No. 61/417,018, filed on Nov. 24, 2010.

(51) Int. Cl.
| | |
|---|---|
| *B82Y 30/00* | (2011.01) |
| *B01J 20/28* | (2006.01) |
| *B01D 53/02* | (2006.01) |
| *B01J 20/22* | (2006.01) |
| *C07F 9/6593* | (2006.01) |

(52) U.S. Cl.
CPC ........ *B01J 20/28073* (2013.01); *B01D 53/02* (2013.01); *B01J 20/22* (2013.01); *B01J 20/226* (2013.01); *B01J 20/28007* (2013.01); *B01J 20/28042* (2013.01); *B01J 20/28057* (2013.01); *B01J 20/28069* (2013.01); *B01J 20/28071* (2013.01); *B01J 20/28092* (2013.01); *B82Y 30/00* (2013.01); *C07F 9/65815* (2013.01); *B01D 2253/20* (2013.01); *B01D 2257/504* (2013.01); *Y02C 10/08* (2013.01); *Y02C 20/20* (2013.01); *Y02P 20/152* (2015.11)

(58) Field of Classification Search
CPC ............... B01D 2253/20; B01D 53/02; B01D 2257/504; B82Y 30/00; C07F 9/65815; Y02C 10/08; Y02C 20/20
USPC ................................... 428/212, 220
See application file for complete search history.

(56) References Cited

U.S. PATENT DOCUMENTS

| | | | |
|---|---|---|---|
| 2005/0109434 A1* | 5/2005 | Seung et al. ........ | 148/561 |
| 2006/0003214 A1* | 1/2006 | Kim et al. ........ | 429/30 |
| 2006/0165574 A1 | 7/2006 | Sayari | |
| 2006/0252641 A1 | 11/2006 | Yaghi | |
| 2008/0038614 A1* | 2/2008 | Nakazawa et al. ....... | 429/30 |
| 2008/0241627 A1* | 10/2008 | Kim ........ | C08G 73/18 |
| | | | 429/494 |
| 2008/0292521 A1 | 11/2008 | Landskron | |
| 2009/0202885 A1* | 8/2009 | Kim et al. ........ | 429/30 |
| 2009/0218220 A1* | 9/2009 | Matter et al. ........ | 204/424 |
| 2010/0029476 A1 | 2/2010 | Trukhan | |
| 2010/0069234 A1 | 3/2010 | Willis | |

OTHER PUBLICATIONS

International Search Report for International Application No. PCT/US2011/031936 mailed Dec. 27, 2011.
Farha, Omar K. et al., "Synthesis, Properties, and Gas Separation Studies of a Robust Diimide-Based Microporous Organic Polymer," Chem. Mater. 2009, vol. 21, pp. 3033-3035.
Written Opinion of the International Searching Authority mailed Dec. 27, 2011 for International Application No. PCT/US2011/031936.

* cited by examiner

*Primary Examiner* — Bijan Ahvazi
*Assistant Examiner* — Lawrence Ferguson
(74) *Attorney, Agent, or Firm* — Saul Ewing LLP

(57) ABSTRACT

Provided herein are synthetic porous electron-rich covalent organonitridic frameworks (PECONFs). The PECONFs are useful as an adsorbent class of materials. In the PECONFs, inorganic nitridic building units are interconnected via electron-rich aromatic units to form porous covalent frameworks. The frameworks include tunable porous, electron-rich organonitridic frameworks, which are determined based upon synthetic methods as exemplified herein.

38 Claims, 20 Drawing Sheets

Table 1

| Sample ID | CO$_2$ uptake (mmol.g$^{-1}$) at 1 atm | | Heat of adsorption for CO$_2$ kJ/mol | CH$_4$ uptake (mmol.g$^{-1}$) at 1 atm | | Heat of adsorption for CH$_4$ kJ/mol | Selectivity for CO$_2$ over N$_2$ | | Selectivity for CO$_2$ over CH$_4$ | | Selectivity for CH$_4$ over N$_2$ | |
|---|---|---|---|---|---|---|---|---|---|---|---|---|
| | 273 K | 298 K | | 273 K | 298 K | | 273 K | 298 K | 273 K | 298 K | 273 K | 298 K |
| PECONF-1 | 1.86 | 1.34 | 29 | 0.83 | 0.53 | 22.2 | 109:1 | 51:1 | 7:1 | 3:1 | 16:1 | 14:1 |
| PECONF-2 | 2.85 | 1.98 | 31 | 1.07 | 0.62 | 26.6 | 74:1 | 44:1 | 9:1 | 5:1 | 8:1 | 8:1 |
| PECONF-3 | 3.49 | 2.47 | 26 | 1.00 | 0.58 | 24.9 | 77:1 | 41:1 | 10:1 | 8:1 | 7:1 | 5:1 |
| PECONF-4 | 2.95 | 1.96 | 34 | 1.07 | 0.67 | 22.5 | 83:1 | 51:1 | 12:1 | 8:1 | 7:1 | 6:1 |

Figure 18

ORGANONITRIDIC FRAMEWORKS WITH HIERARCHICAL PORE STRUCTURES AND HIGH GAS SELECTIVITY

CROSS-REFERENCE TO RELATED APPLICATIONS

This application is a 371 national stage application of PCT/US2011/031936, filed Apr. 11, 2011, which claims the priority of U.S. Provisional patent application No. 61/322,581, filed on Apr. 9, 2010, and U.S. Provisional patent application No. 61/417,018, filed on Nov. 24, 2010, each of which are incorporated herein by reference in their entireties.

Not Applicable

BACKGROUND

A large fraction of the electricity use in the United States is generated by coal-fired power plants. Such combustion powered plants, and other emission sources, produce carbon dioxide in large amounts, and collectively in the billion ton scale. Effective materials and methods are required for the capture of carbon dioxide in order to reduce environmental pollution, and to comply with existing and proposed environmental laws and regulations. There exists a tremendous and unmet need for new technologies that effectively and efficiently separate carbon dioxide from other gases for environmental uses and reasons, as well as for any other application in which carbon dioxide is required to be separated and isolated from other gases.

For all those reasons, carbon dioxide capture from point sources like coal-fired power plants is considered desirable. However, separation of $CO_2$ from flue gas to date has been difficult to accomplish in a cost-efficient, low-waste manner. Methods and sorbents with high gas selectivity, good chemical and thermal stability, low cost, and reversible adsorption are desired.

Flue gas emitted from coal-fired power plants constitutes 15-16% $CO_2$, 6-7% $H_2O$, 3-4% $O_2$, and about 70% $N_2$[1]. Carbon dioxide capture from coal-fired power plant emitters is currently considered as a possible technology to stabilize the $CO_2$ level in the atmosphere. A variety of sorbent materials are currently under investigation for carbon dioxide capture. Porous materials have been generally discussed as possible sorbents for carbon dioxide capture. Several classes of porous materials are currently under investigation, predominantly metal-organic frameworks (MOFs), activated carbons, molecular organic solids, and amine-functionalized silicas. More recently, research has begun on $CO_2$ sorption involving covalent organic frameworks. Generally, sorbents which physisorb $CO_2$ (e.g. MOFs and carbons) tend toward lower selectivity and sorption capacity at low $CO_2$ pressure (≤1 atm) but exhibit facile reversibility. In comparison, strongly chemisorbing materials such as amine-functionalized silicas tend towards higher selectivities and capacities but typically show less facile reversibility. Recently, amine-functionalized MOFs have been reported that exhibit increased $CO_2$ sorption at low pressure as well as significantly improved selectivity. Still, MOFs tend toward chemical instability (oxidation, hydrolysis) due to the dative nature of the metal-ligand bonds. It is apparent that inexpensive sorbents with enhanced chemical stabilities and heats of adsorption at the borderline between strong physisorption and weak chemisorption (ca. 25-50 kJ/mol) remain an attractive, yet unmet, target to provide adsorbents having the desirable properties identified herein.

SUMMARY

Provided herein are novel materials having a high sorption activity and selectivity for carbon dioxide, and methods for using the materials. For example, the materials described herein have very favorable characteristics for effective separation of carbon dioxide from other gases. Desirable characteristics include, but are not limited to: sorption capacities, gas selectivity, stability, longevity, inexpensive synthesis and manufacture, among other things.

In one embodiment, the materials include an organonitridic composition, wherein the composition comprises a plurality of inorganic nitridic units interconnected by aromatic units, and wherein the composition further comprises a porous framework.

BRIEF DESCRIPTION OF THE DRAWINGS

FIG. 18 illustrates various chemical and physical properties of exemplary PECONF materials herein.

DETAILED DESCRIPTION

Figure 1:
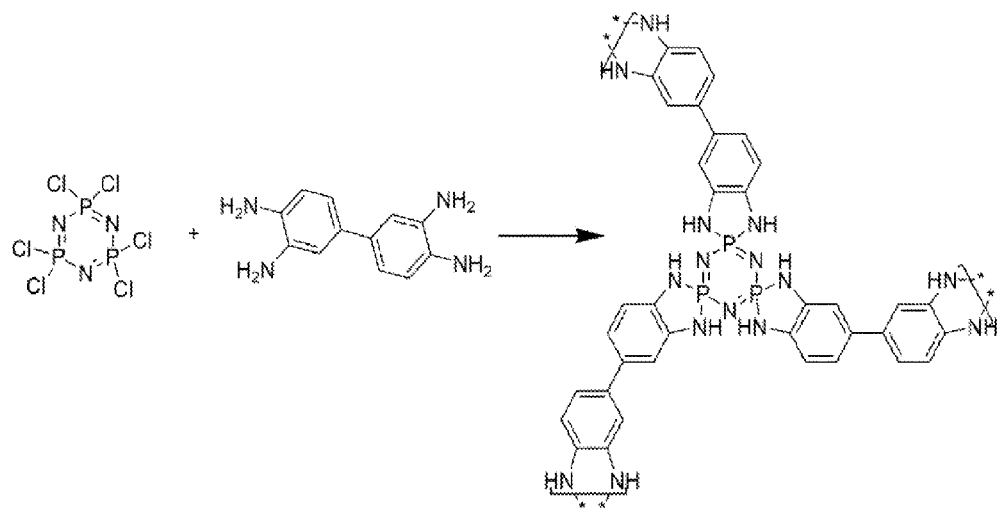
FIG. 1 illustrates a reaction scheme embodiment of the methods herein.

The present invention provides methods for preparing and using novel materials having desirable adsorbent properties. The novel sorbent materials herein are useful in any application involving separation and/or removal of gases. For example, the inventors have determined that the materials provide all of inventor-determined desirable features of sorbents suitable for carbon dioxide capture from exhaust streams, including: high selective sorption capacity for $CO_2$; facile regeneration of the sorbent at low energy penalty; low cost of the sorbent material; chemical stability of the sorbent towards $H_2O$, $O_2$ as well as good thermal stability. The sorbents described herein have those key features and characteristics and have been shown to be efficient and selective for adsorption of $CO_2$ and methane from gaseous combustion exhaust streams. Preferably, the adsorption of $CO_2$ and methane is not accompanied with simultaneous adsorption of significant amounts of gases such as nitrogen.

With those key features in mind, the inventors have synthesized porous electron-rich covalent organonitridic frameworks (PECONFs). The PECONFs herein constitute a novel new material and are also useful as an adsorbent class of materials. In PECONFs, inorganic nitridic building units are interconnected via electron-rich aromatic units to form porous covalent frameworks. The frameworks are characterized herein, and include tunable porous, electron-rich organonitridic frameworks. A number of archetypes of PECONFs are provided herein, as well as methods for creating each archetype. For example, exemplary PECONFs were prepared by simple condensation reactions between inexpensive, commercially available nitridic and electron-rich aromatic building units. The PECONF materials exhibit high and reversible $CO_2$ sorption capacity up to 3.5 mmol·g$^{-1}$ (at 273 K and 1 atm) and exceptional gas selectivity up to 109:1 ($CO_2$:$N_2$) at the zero pressure limit. The isosteric heat of adsorption of the materials is nearly independent from the $CO_2$ loading and reaches values of up to 35 kJ·mol$^{-1}$. The PECONF materials do not oxidize in air up to temperatures of at least about 400° C. The PECONF materials are characterized by micropores ("micropores" means pores having a diameter of less than about 2 nm), with some embodiments also including macropores ("macropores" means pores having a diameter of greater than about 50 nm). As used herein, "mesopores" means pores having a diameter of greater than about 2 nm to less than about 50 nm. Pore size, pore volume, and surface of the PECONF materials can be controlled during material formation, as further described herein. Thus, the structures are "tunable" for control of such features in the final PECONF formed in any given batch. While many embodiments herein discuss the PECONF materials as adsorbents useful as selective solid gas sorbents, other uses such as filtration, membranes, retention, and delivery of materials can be readily discerned based upon the properties of the materials described herein. Additionally, the materials in several embodiments herein are substantially non-conductive or insulating with respect to thermal and electrical energy.

Without being limited to any theory as to why the PECONF materials are such excellent gas adsorbents and gas separators (some embodiments are also gas separation membranes), it is believed that carbon dioxide sorption is facilitated or enhanced in the PECONFs due to Lewis-acid Lewis-base interactions between the electron-rich aromatic constituents of the framework and the electron-poorer carbon dioxide molecules of the targeted exhaust stream. In addition, weak Lewis acid-base interactions between the lone pairs at the nitridic building units and $CO_2$ could contribute. Both types of interactions are likely stronger than simple physisorptive van der Waals interactions (5-20 kJ/mol) but weaker than strong chemisorptive interactions (>50 kJ/mol) because no covalent bonds are formed between the sorbent and $CO_2$. The covalent and inert nature of the bonds in PECONFs suggests high chemical stability. In testing to date, as described herein, that stability has been shown.

Figure 8:
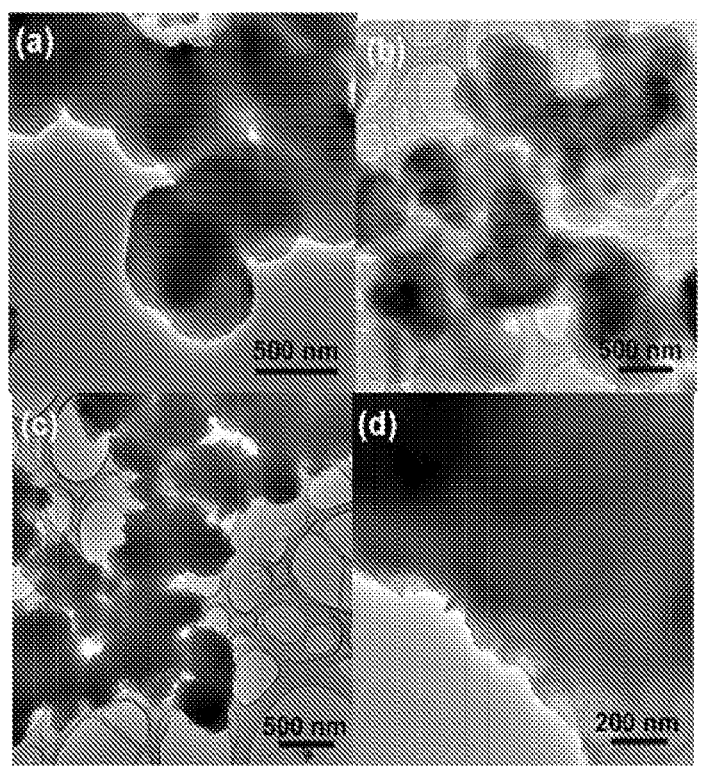
FIG. 8 illustrates transmission electron micrographs of PECONF materials herein.

We have produced archetypes of porous covalent organophosphonitridic frameworks (PECONFs) from inexpensive 3,3'-diaminobenzidine (DAB) and phosphonitrilic chloride trimer (PNC) in simple polycondensation reactions using DMSO as the solvent. FIG. 1 shows an exemplary reaction scheme for the synthesis of the novel PECONF materials. Without being limited by theory, in that reaction scheme, DAB acts as the electron-rich aromatic building block due to its four amino groups while PNC plays the role of the nitridic building unit. The reaction product materials were obtained as monoliths, which could be solvent-exchanged and dried without cracking or disintegration. The microstructures of the monoliths can be controlled or modulated, such as by systematically decreasing the amount of the solvent (DMSO) in the reaction mixture. In an example herein, the Scanning Electron Micrograph ("SEM") of FIG. 2 and a corresponding Transmission Electron Micrograph ("TEM") of FIG. 8 show that the PECONFs materials are composed of inter grown, nearly spherical particles. The diameter of the spheres appears to be a function of the reactant concentration. For example, PECONF-1, which was synthesized at the highest concentrations, showed the largest spheres with diameters around 600 nm. PECONF-2 and PECONF-3, which were synthesized at decreased reactant concentrations but otherwise similar conditions as PECONF-1, exhibited decreased sphere diameters of around 400 and 200 nm, respectively. The moderate intergrowth of the spheres results in or produces macropores between the spheres. PECONF-4, which was produced at the lowest reactant concentrations, has a polygranular structure with grain sizes in the order of a few tens of nanometers. Notably, PECONF-4 does not exhibit macroporosity. All of the PECONF-1, PECONF-2, PECONF-3, and PECONF-4 materials were non-crystalline according to powder X-ray diffraction ("XRD"), as shown in exemplary FIG. 9, and as observed by the inventors in selective area electron diffraction ("SAED") testing.

Figure 3A:
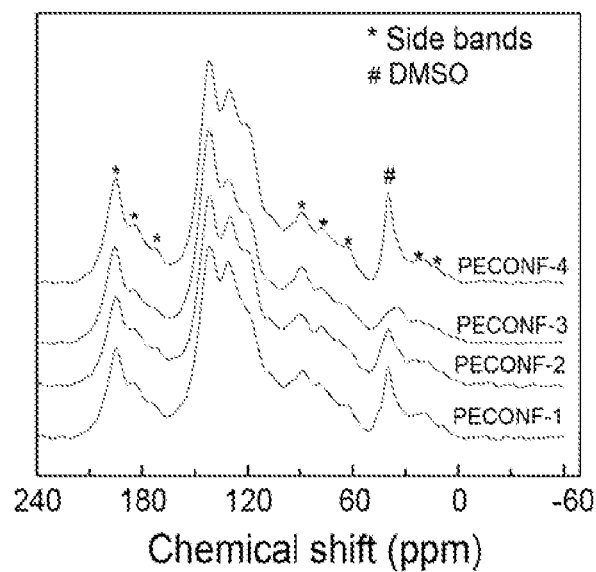
FIG. 3 illustrates NMR spectra of PECONF materials herein.

To investigate the structure of the materials in more detail, we have studied the P MAS NMR and C CP MAS NMR spectra of the PECONFs. FIG. 3a shows the C spectra of exemplary PECONFs. Strong signals around 141 and 131 ppm with a shoulder at 121 ppm and a small weak signal at 106 ppm were observed in the C CP-MAS spectra. The chemical shifts are consistent with the presence of the DAB building block. This confirms that the electron-rich aromatic DAB unit was incorporated into the PECONF materials. An additional signal was observed around 39 ppm, which can be attributed to residual DMSO that was used as the solvent for the synthesis.

Figure 3B:
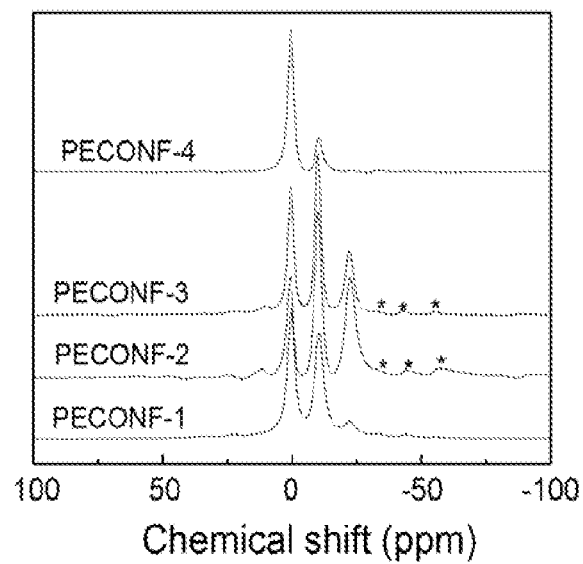

The P MAS-NMR spectra (FIG. 3b) of the PECONFs showed signals in the range from 0 to −25 ppm, which are typical for P(V)$N_4$ tetrahedra. In PECONF-1, two strong, and a weak signal were observed at 0.4, −10.4, and −22.5 ppm, respectively. In PECONF-2, 3, and 4, three signals at almost identical chemical shifts were seen. All the signals were astonishingly sharp given that all the materials were non-crystalline. This indicated that the materials have not only short-range but also mid-range order. The observation of three signals suggests that three different phosphorus environments are present in the frameworks. This may be explained by the fact the P atoms can be surrounded by bridging as well as terminal DAB units in the framework.

Figure 10:
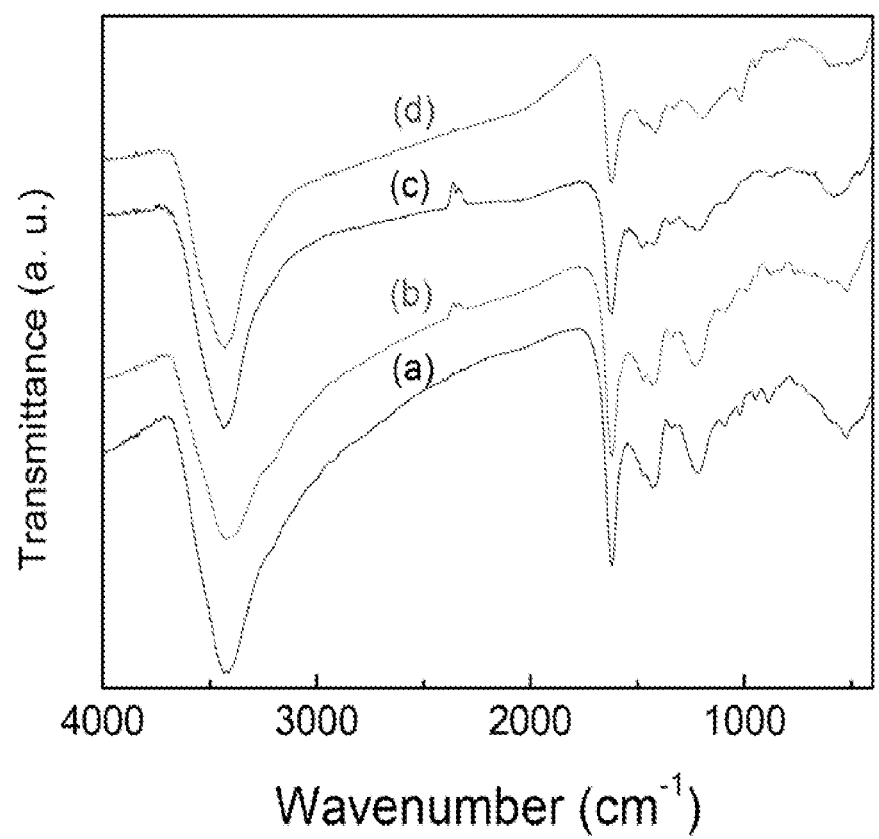
FIG. 10 illustrates FT-IR spectra of PECONF materials herein.
Figure 11A:
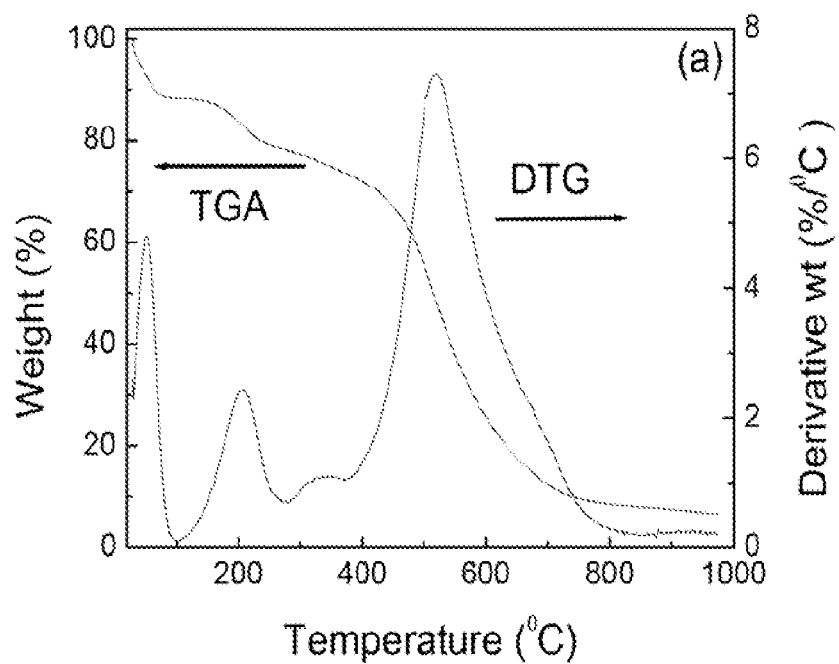
FIG. 11 illustrates TGA and DTG thermograms in air of PECONF materials herein.
Figure 11B:
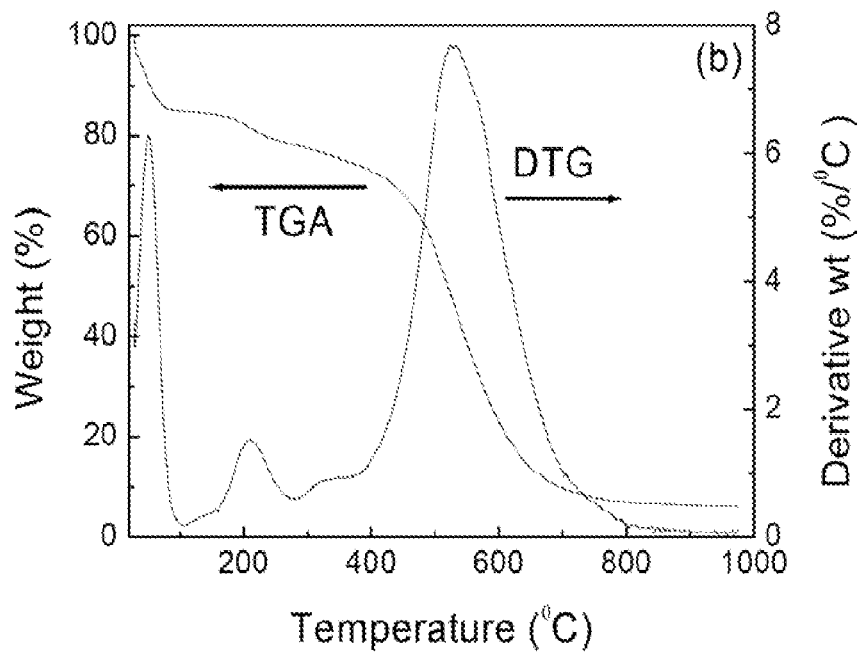
Figure 11C:
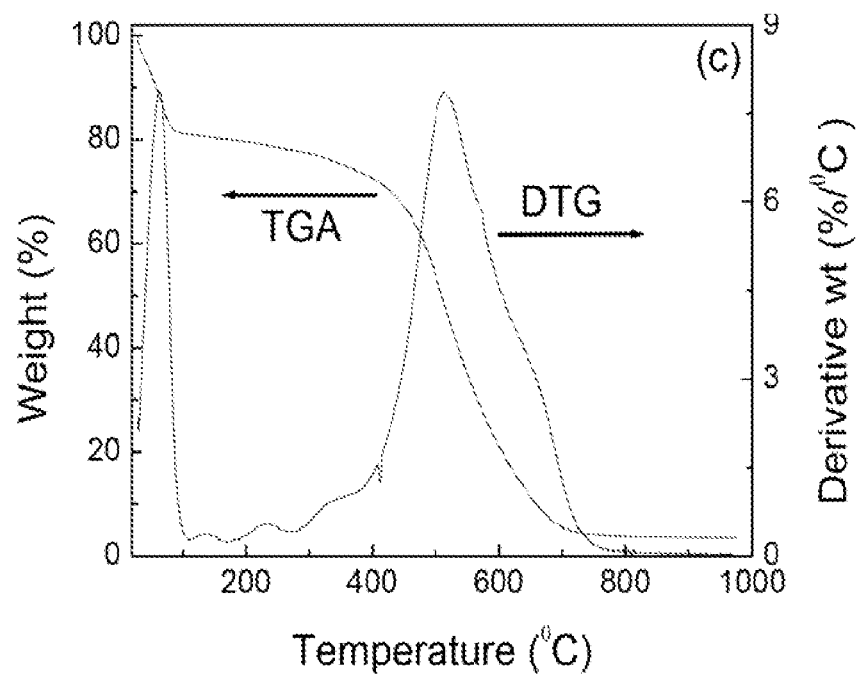
Figure 11D:
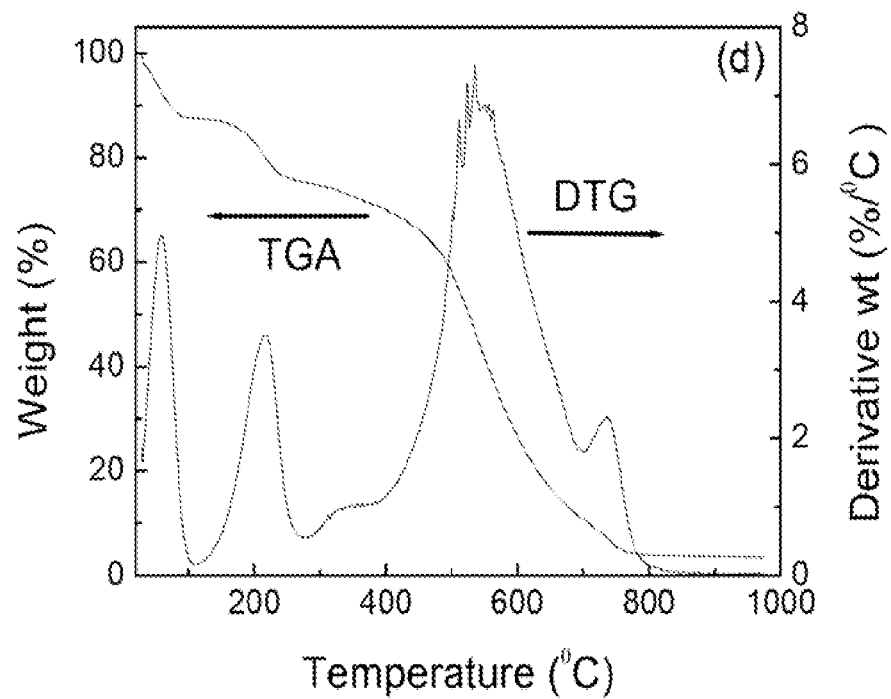
Figure 12A:
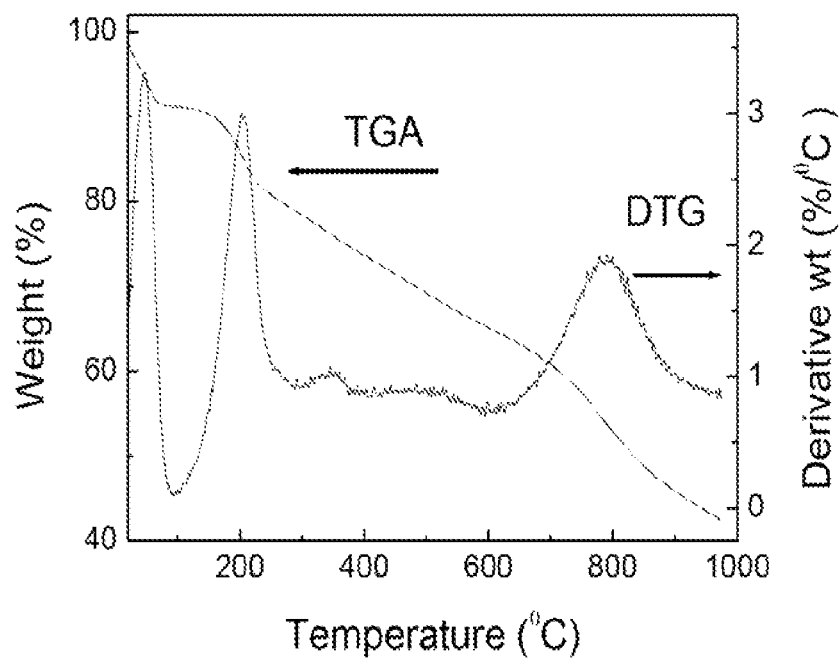
FIG. 12 illustrates TGA and DTG thermograms in nitrogen of PECONF materials herein.
Figure 12B:
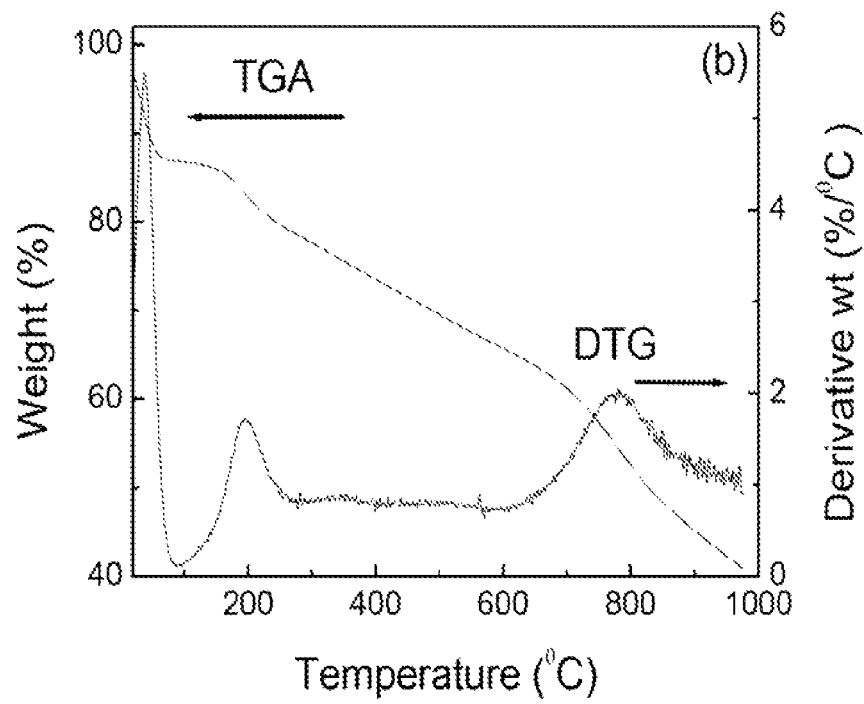
Figure 12C:
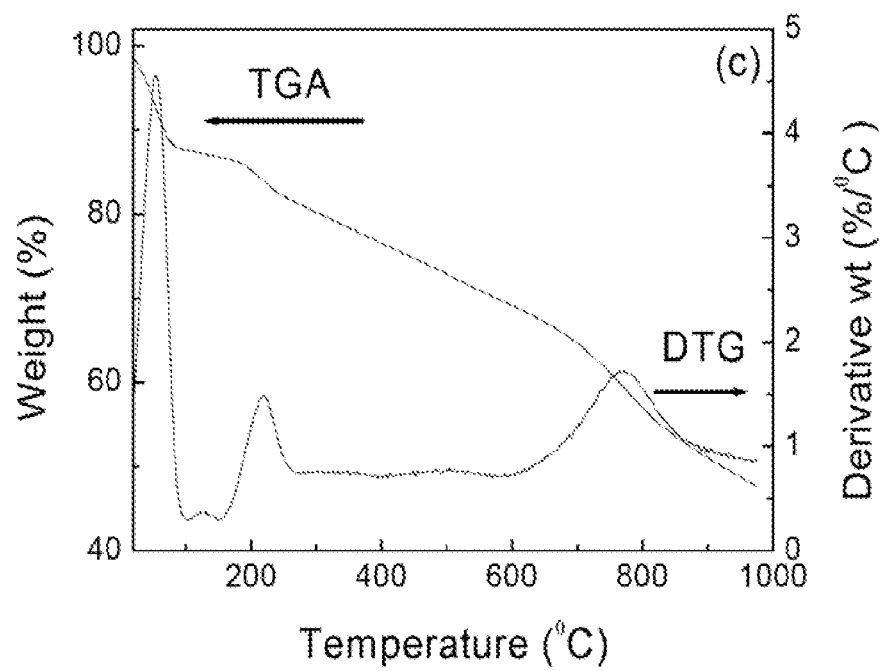
Figure 12D:
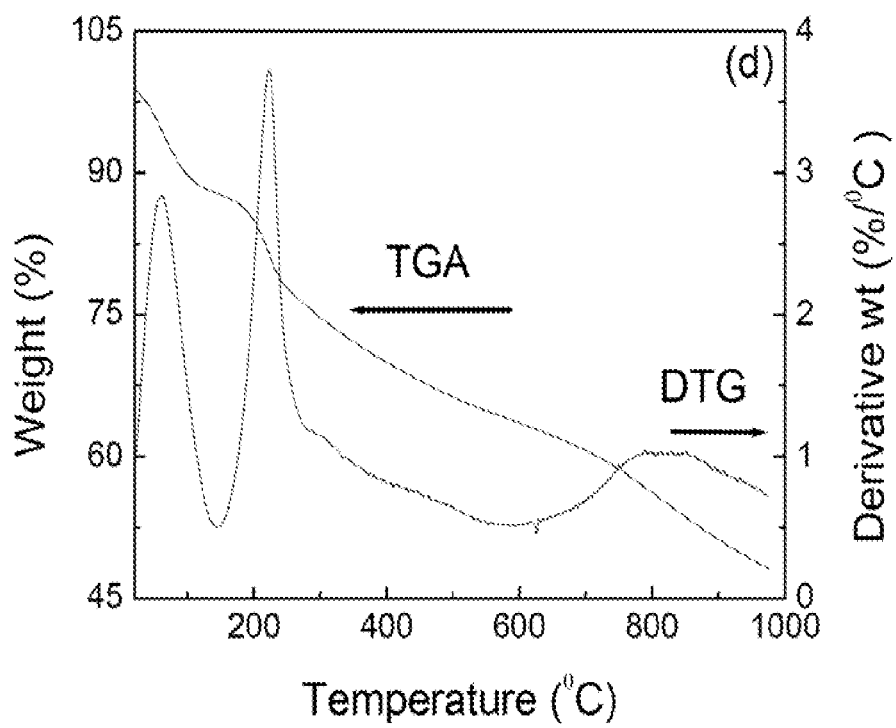

The PECONF materials were further studied by FT-IR spectroscopy (FIG. 10). All the spectra shows a broad band around 3420 cm$^{-1}$ and a sharp band around 1617 cm$^{-1}$. These bands can be attributed to the N—H stretching and bending vibrations, respectively. Furthermore, several broad bands are observed in the region from 1500 to 500 cm$^{-1}$. The bands at ~1090 and ~950 cm$^{-1}$ can be attributed to the $v_{as}$(P—NH—P) vibrations. The bands at 1218 and 1420 cm$^{-1}$ are due to the $v_{as}$(P=N—P) vibrations. The band around 520 cm$^{-1}$ can be assigned to the δ(P=N—P) vibrations. Similar bands are also observed in phosphorus nitride, nitride imides, and oxynitrides. The sharpness of the bands in the fingerprint region suggests a high degree of mid-range order in the materials which corroborates the results from P MAS NMR spectroscopy.

We further studied the thermal behavior and the oxidative stability of the PECONFs. FIG. 11 shows the TGA and DTG thermograms of PECONFs. The materials are thermally stable up to a temperature of 400° C. in air. The thermograms show that mass loss occurs in four steps. The first two steps (mass loss ~20%) below 300° C. are attributed to the desorption of small amounts of water and occluded DMSO (the presence of DMSO was confirmed from the C MAS-NMR). Only above 400° C. continuous mass loss was observed that can be attributed to oxidation and framework decomposition (FIG. 11). The mass loss at ~500° C. can be attributed to the oxidation of the organic units. Furthermore, a shoulder was observed at ~700° C. which is due to the decomposition of the P—N units. The TGA thermograms of the samples heated in $N_2$ environment are shown in FIG. 12. All the thermograms show a three step mass loss with a total mass loss of about 60%. The first two steps were observed below 300° C. and are attributed to desorption of small amount of water and occluded DMSO. Unlike the sample heated in air, no significant mass loss was observed between 400 to 600° C. This confirmed that the mass loss at ~500° C. in air is due to the oxidation of the organic units. The materials are thermally stable up to a temperature of 600° C. in $N_2$ atmosphere. The decomposition of the P—N units did not occur below 800° C. in $N_2$.

Figure 4A:
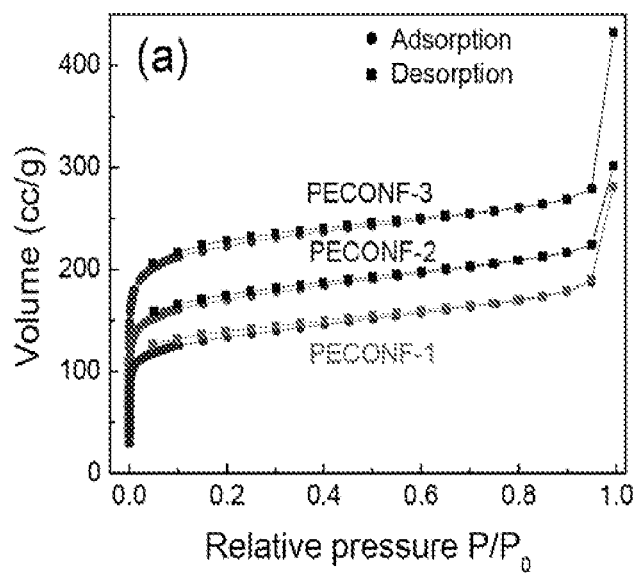
FIG. 4 graphically illustrates sorption of PECONF materials herein.

In order to probe for porosity in the PECONFs, we recorded $N_2$ isotherms at 77 K. FIG. 4a shows the $N_2$ sorption isotherms of PECONF-1, PECONF-2, and PECONF-3. All of these materials show a type-I isotherm, which is typical for microporous materials. The surface area of these samples increases systematically from PECONF-1 to PECONF-3. The Langmuir surface areas were estimated to be 583, 742 and 969 m$^2$·g$^{-1}$ for PECONF-1, PECONF-2 and PECONF-3, respectively (Table 1). These values are further comparable with the cumulative surface areas (559, 717, and 939 m$^2$·g$^{-1}$ for PECONF-1, PECONF-2 and PECONF-3, respectively) calculated by DFT & Monte-Carlo analysis (Table 1). The calculated Brunauer-Emmett-Teller (BET) surface areas (499, 637, and 851 m$^2$·g$^{-1}$ for PECONF-1, PECONF-2 and PECONF-3, respectively) have somewhat lower values compared to the corresponding Langmuir surface areas. The pore volumes estimated at p/p$_0$=0.95 are 0.290, 0.348 and 0.434 cm$^3$·g$^{-1}$ for PECONF-1, PECONF-2 and PECONF-3, respectively. Details about the physicochemical properties are given in Table 1. No hysteresis was observed between p/p$_0$ of 0.4 and 0.85 in these materials confirming the absence of mesopores. The sharp $N_2$ uptake above p/p$_0$=0.95 confirms the macroporosity, which was already seen by TEM and SEM. The isotherms are not completely closed yet at p/p$_0$=0.2. A similar non-closed isotherm for a non-crystalline covalent organic framework was recently observed by Huppet. al.

Figure 4B:
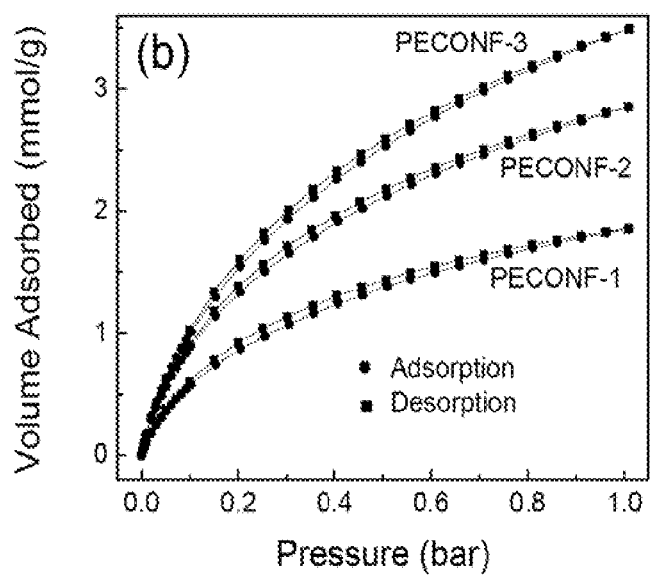

The microporous nature and the high surface area of PENCONF-1, 2, and 3 prompted us to study their $CO_2$ sorption properties. FIG. 4b shows the $CO_2$ sorption isotherms of PECONF-1, PECONF-2, and PECONF-3 measured at 273 K. For all materials, the $CO_2$ sorption was completely reversible and no significant hysteresis was observed. The $CO_2$ uptake of PECONF-1, PECONF-2, and PECONF-3 reaches values of 1.86, 2.85 and 3.49 mmol g$^{-1}$, respectively at 1 atm. The cumulative surface areas calculated from the $CO_2$ isotherm at 273 K using DFT & Monte-Carlo analysis show values of 438, 670, and 827 m$^2$·g$^{-1}$ for PECONF-1, PECONF-2 and PECONF-3, respectively (See Table of FIG. 18). These values are somewhat lower compared to the surface areas calculated from the $N_2$ sorption data of these materials using the Langmuir equation. The results indicate that the $CO_2$ sorption capacity scales with the surface area of the material and is inverse proportional to the reactant concentration in the synthesis.

Figure 4C:
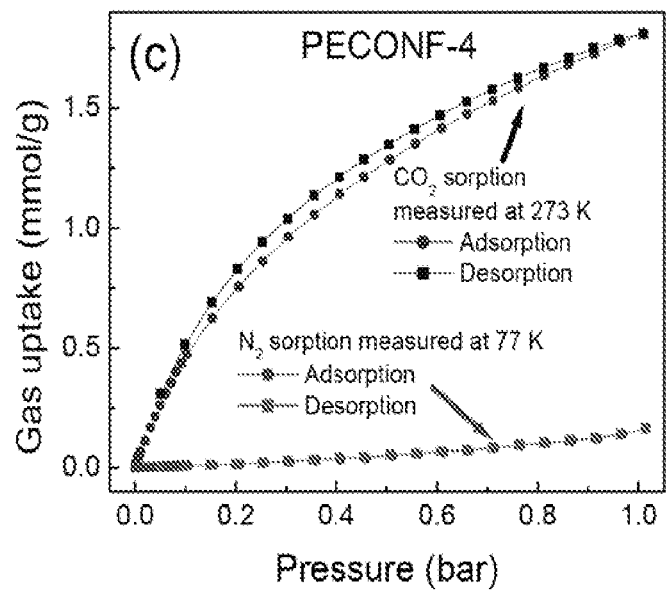
Figure 4D:
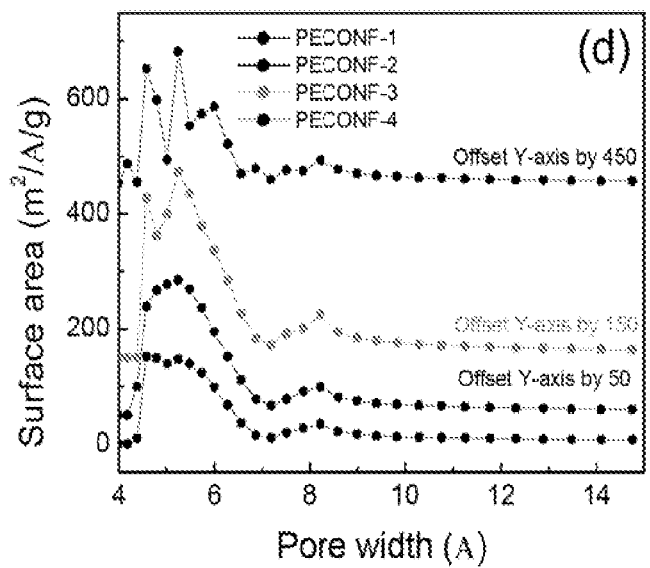

PECONF-4 in monolithic form adsorbed only very small amounts of $N_2$ at 77 K (FIG. 4c) and was practically non-porous for $N_2$. Surprisingly however, it had a relatively large $CO_2$ uptake of 1.81 mmol·g$^{-1}$ at 273 K (FIG. 4c). This can be explained by the slow mass transport of $N_2$ into the PECONF-4 micropores at 77 K. The surface area and the pore volume calculated from the $CO_2$ sorption isotherm of this material using Density Functional Theory showed values of 433 m$^2$·g$^{-1}$ and 0.14 cm$^3$·g$^{-1}$, respectively. The $CO_2$ uptake is remarkable given the small pore volume of only 0.14 mmol·g$^{-1}$. In fact, PECONF-4 has the highest sorption capacity to pore volume ratio of all PECONF materials. The pore size distributions (PSDs) of PECONF-1 to PECONF-4 estimated from the $CO_2$ sorption using DFT theory are shown in FIG. 4d. PECONF-1 and PECONF-2 have a narrow monomodal pore size distribution centered on 0.55 nm. PECONF-3 begins to exhibit a bimodal pore size distribution. PECONF-4 is clearly bimodal. For PECONF-4 a small additional small maximum is observed at 0.62 nm.

Figure 5:
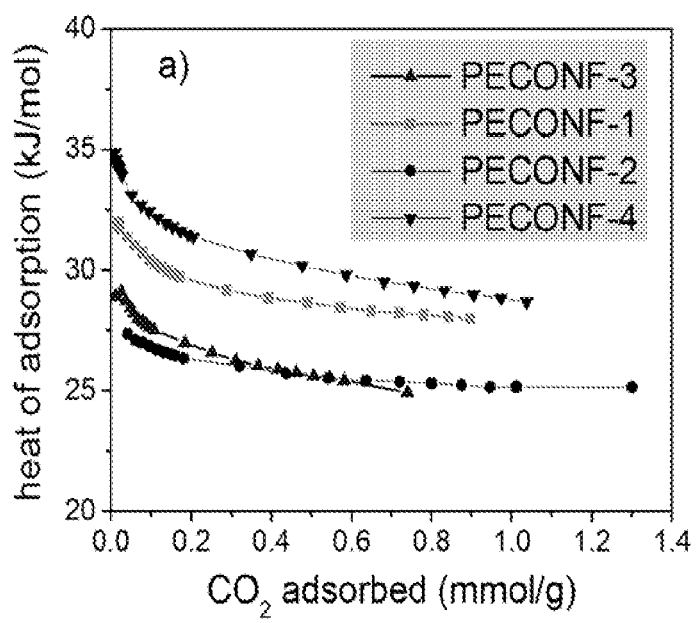
FIG. 5 graphically illustrates heat of adsorption of PECONF materials herein.

In order to further understand the pore surface characteristics of the materials and the $CO_2$ adsorption process, we have calculated the isosteric heats of $CO_2$ adsorption (ΔH). ΔH was calculated using the Clausius-Clapeyron equation from the sorption data collected at 273 and 298 K. The ΔH value can be obtained from the plot of 1 np versus the reciprocal of the temperature. FIG. 5 shows ΔH of PECONF-1 to PECONF-4. At the adsorption onset, the ΔH values for PECONF-1, PECONF-2, PECONF-3, and PECONF-4 are 32, 27, 29, and 35 kJ·mol$^{-1}$, respectively (FIG. 5). Remarkably, the isosteric heat of adsorption is nearly independent from the amount of $CO_2$ adsorbed. The heats of adsorption for PECONF-1, 2, 3, and 4 drops only by 30%. This suggests that if the pore volumes of the materials can be further increased, a significantly higher $CO_2$ sorption capacity can likely be achieved even at low $CO_2$ pressure.

Figure 6A:
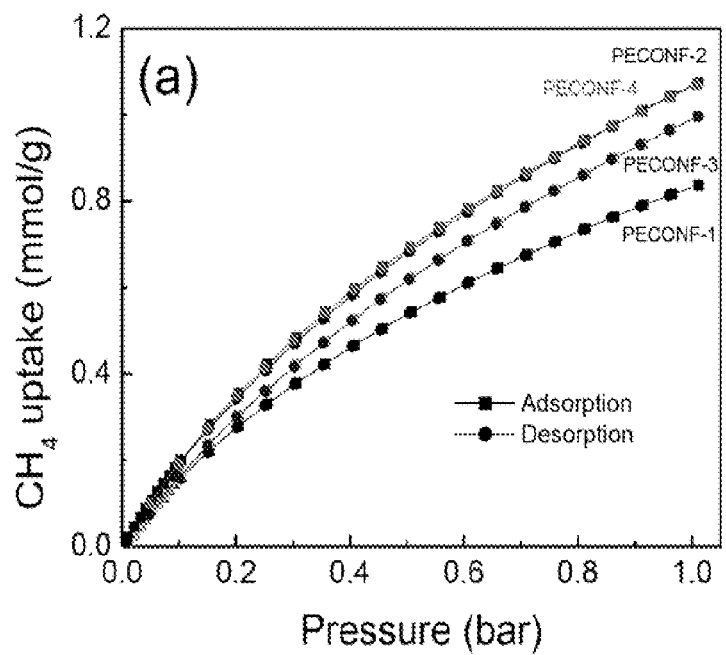
FIG. 6 graphically illustrates adsorption and sorption of PECONF materials herein.
Figure 6B:
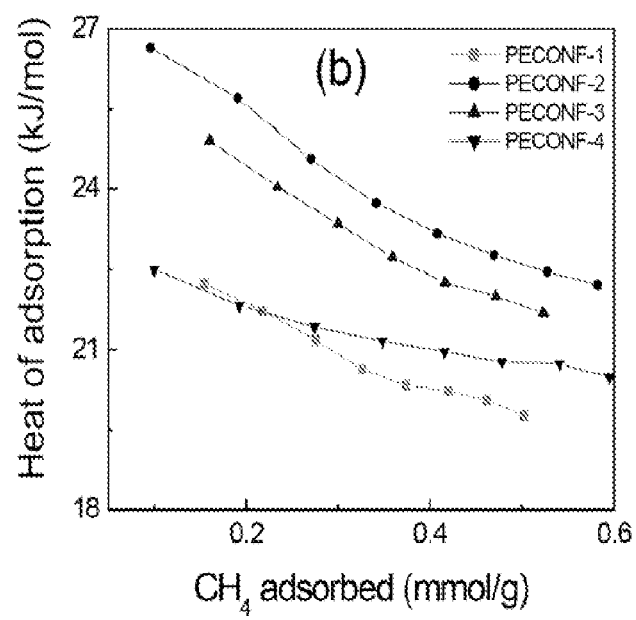
Figure 13:
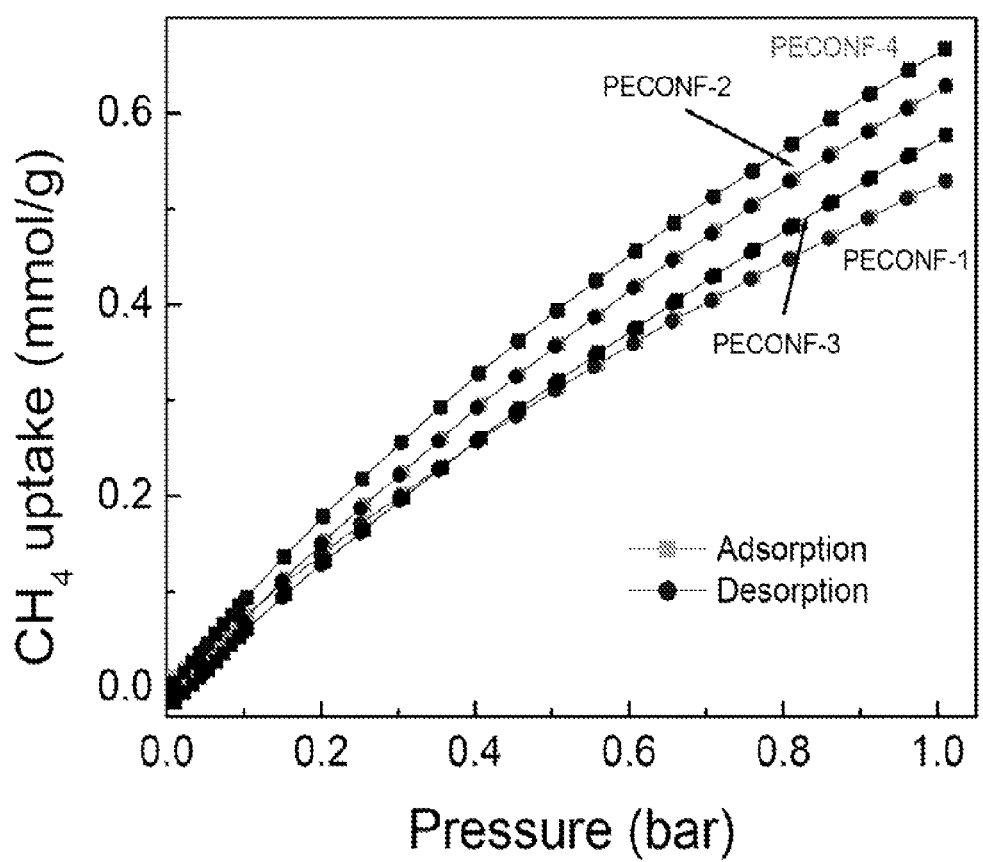
FIG. 13 illustrates methane sorption isotherms (298 K) of PECONF materials herein.

We have further studied the methane sorption behavior of the PECONF materials in pulverized form. FIG. 6a shows the $CH_4$ sorption isotherms of the PECONF-1 to PECONF-4. All the isotherms are reversible with a very high maximum uptake of 1.07 mmol/g observed for PECONF-2 and PECONF-4 at 1 bar and 273 K. The PECONF-3, which has the highest surface area and maximum $CO_2$ uptake, adsorbs a somewhat smaller amount (1 mmol/g) of methane. PECONF-1 has the lowest $CH_4$ sorption capacity of 0.83 mmol/g. The methane uptake capacities of these samples are still high at 298 K with the maximum uptake of 0.67 mmol/g at a pressure of 1 bar observed for PECONF-4. The methane sorption capacities of PECONF-1, PECONF-2, and PECONF-3 are 0.53, 0.63, and 0.58, respectively at 298 K (FIG. 13). We further calculated the isosteric heat of adsorption of the methane for all the samples. FIG. 6b shows ΔH of PECONF-1 to PECONF-4. At the adsorption onset, PECONF-1, PECONF-2, PECONF-3, and PECONF-4 show very high values of 22.2, 26.6, 24.9, and 22.5 kJ·mol$^{-1}$, respectively. The heat of adsorption only weakly decreases with increasing methane loading. It is noteworthy that, with the exception of PECONF-4, the methane sorption capacity is increasing with increasing heat of adsorption, while the $CO_2$ sorption capacity increases with the surface area. Apparently in the case of methane adsorption, the heat of adsorption is more important than the surface area. The "abnormal" behavior of the PECONF-4 for both the $CO_2$ and the $CH_4$ sorption behavior may be associated with its different microstructure. The generally high methane uptake for all PECONFs may be explained by H-π interactions. Such interactions have been observed in Van der Waals crystals of tris-o-phenylenedioxycyclotriphosphazene molecules, that are structurally related to the building units of the PECONF materials.[x]

TABLE 1

Physicochemical properties of PECONF materials.

| Sample ID | Surface area from $N_2$ sorption at 77K $(m^2 \cdot g^{-1})$ | | DFT & Monte-Carlo Cumulative surface area $(m^2 \cdot g^{-1})$ | | DFT & Monte-Carlo Cumulative pore volume $(cm^3 \cdot g^{-1})$ | | Total pore volume ($N_2$ at 77K $(cm^3 \cdot g^{-1})$) |
|---|---|---|---|---|---|---|---|
| | BET | Langmuir | $N_2$ at 77K | $CO_2$ at 273K | $N_2$ at 77K | $CO_2$ at 273K | |
| PECONF-1 | 499 | 583 | 559 | 438 | 0.314 | 0.133 | 0.290 |
| PECONF-2 | 637 | 742 | 717 | 670 | 0.356 | 0.202 | 0.348 |
| PECONF-3 | 851 | 969 | 939 | 827 | 0.468 | 0.257 | 0.434 |
| PECONF-4 | — | — | — | 433 | — | 0.139 | — |

Figure 16A:
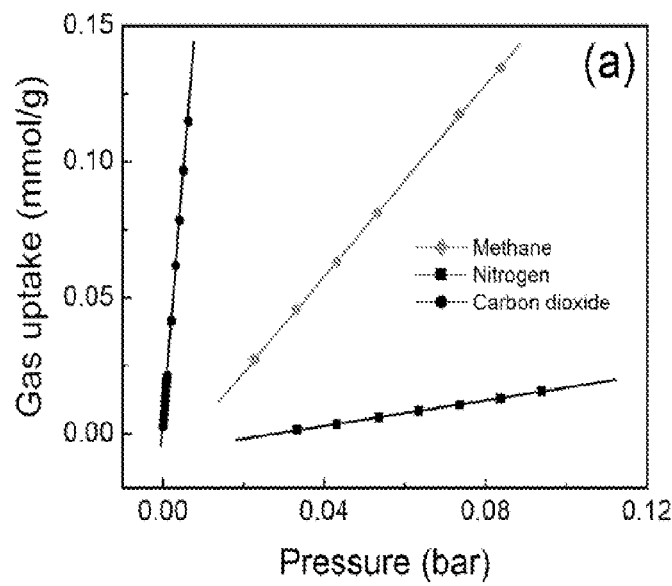
FIG. 16 illustrates the nitrogen, methane, and carbon dioxide sorption of PECONF-3 material herein.
Figure 16B:
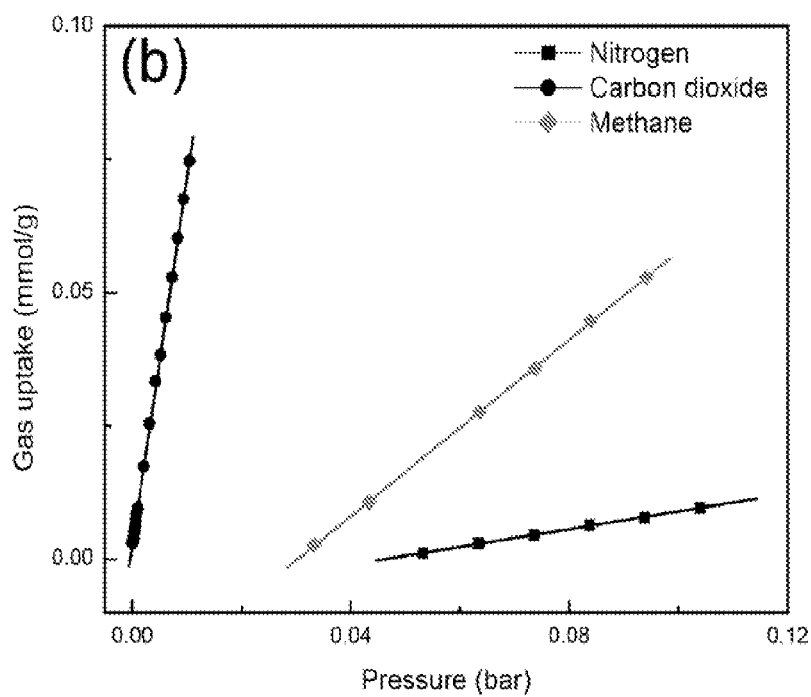
Figure 17A:
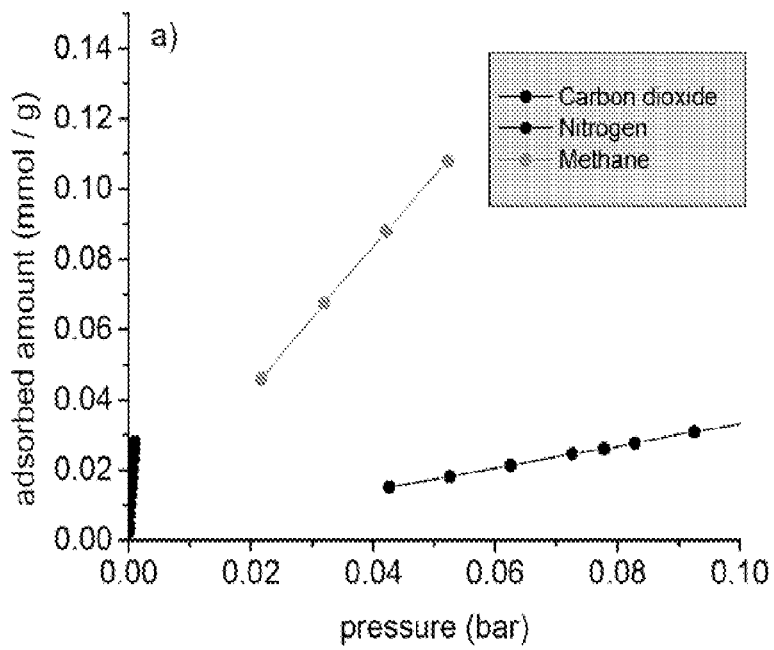
FIG. 17 illustrates the nitrogen, methane, and carbon dioxide sorption of PECONF-4 material herein.
Figure 17B:
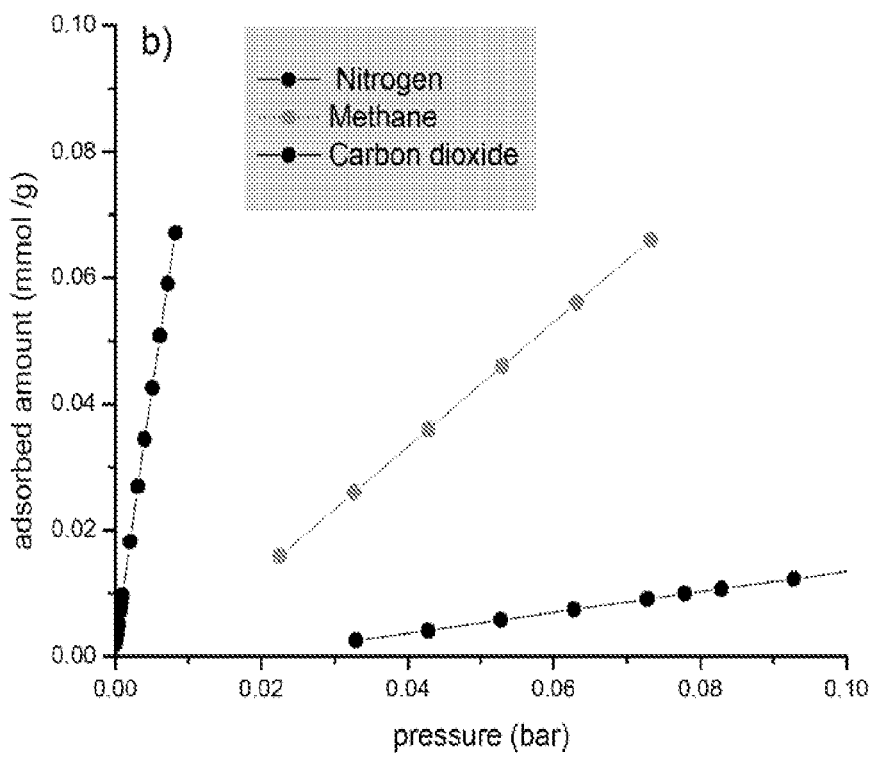

In addition to the high $CO_2$ uptake and the reversibility, a high selectivity for $CO_2$ over $N_2$ is one of the necessary properties for a material to be used as a $CO_2$ adsorbent. In order to estimate the selectivity for $CO_2$ over $N_2$, we measured the $CO_2$ and $N_2$ sorption isotherms at 273 K and 298 K. The selectivity was estimated using the ratios of the Henry law constants. These constants can be calculated from the initial slopes of the isotherms. This method is the most common method to calculate gas selectivity and has been applied extensively to determine gas selectivity of metal-organic frameworks, carbons, and covalent organic frameworks. The calculated $CO_2$:$N_2$ selectivity of PECONF-1 is the highest among the PECONF materials reaching values of 109:1 at 273 K and 51:1 at 298 K (See Table 1 of Figure, 18, FIG. 7 and FIG. 14). To our best knowledge, this is the highest value measured for any physisorbent with a reversible isotherm. The value is much higher compared to the next-higher value reported so far (81:1 at 273 K). The $CO_2$:$N_2$ selectivities for PECONF-2 (FIG. 7 and FIG. 15) and PECONF-3 (FIG. 16) are still high (PECONF-2: 74:1 and 44:1 at 273 and 298 K, PECONF-3: 77:1 and 41:1 at 273 and 298 K). The higher selectivity of PECONF-1 compared to PECONF-2, and 3 can be attributed to its higher heat of adsorption. PECONF-4 has a selectivity of 83:1 and 51:1 at 273 and 298 K, respectively (FIG. 17).

We further calculated the selectivity of $CO_2$:$CH_4$ and $CH_4$:$N_2$ of these samples at 273 and 298 K (Table S1, FIG. 7, FIG. 14-17). PECONF-4 has the highest $CO_2$:$CH_4$ selectivity of 12 at 273 K among all the materials. However, the $CH_4$:$N_2$ selectivity of 16 is maximum for the PECONF-1 at 273 K. Sorbents with high selectivity for $CH_4$ over $N_2$ are of high practical interest because methane is often highly diluted by $N_2$ in natural gas wells. Currently, $N_2$/$CH_4$ separations are still being done cryogenically because of the absence of solid sorbents with high methane sorption capacities and suitable selectivities.

In summary, we have synthesized microporous electron-rich covalent organonitridic frameworks in facile condensation reactions from commercially available inexpensive building blocks (DAB and PNC). The structures are tunable despite their non-crystallinity and exhibit a remarkable degree of mid-range order. The hierarchical micro-macroporosity is a further advantageous feature of the materials due the benefits of hierarchical porosity for the mass transport in porous materials. The tunability of the structures translates to their gas sorption properties. The materials adsorb high amounts of $CO_2$ (up to 3.5 mmol·$g^{-1}$) which is exceeded by only a few other sorbents, namely the amine-functionalized silica MBA-2 (3.8 mmol), and the amine-functionalized MOFs bio-MOF-11 (6.0 mmol $g^{-1}$), $Zn_2(C_2O_4)(C_2N_4H_3)_2 \cdot (H_2O)_{0.5}$ (4.35 mmol $g^{-1}$), and Mg/DOBDC (7.2 mmol·$g^{-1}$). To our best knowledge, the material PECONF-1 exhibits the highest calculated selectivity ($CO_2$ over $N_2$) of a sorbent with a reversible $CO_2$ adsorption-desorption isotherm. The high isosteric heat of adsorption and the high selectivity for $CO_2$ over $N_2$ can be explained by Lewis acid-base interactions between the electron-poor $CO_2$ and the electron-rich sorbent. The heats of adsorption do not decline significantly even at high $CO_2$ loadings. Similarly high isosteric heats of adsorption have been observed only for metal-organic frameworks but not for covalent framework materials composed exclusively from non-metals. The strong covalent P—N, N—C, and C—C bonds in the framework provide the materials with high chemical robustness compared with MOFs as seen by the high oxidative stability at temperatures as high as 400° C. The combination of high thermal and oxidative stability, high sorption capacity, low cost, and exceptional selectivity for $CO_2$ over $N_2$ make these materials interesting candidates for $CO_2$ capture applications.

Furthermore, the PECONF materials show high sorption capacities and heats of adsorption for methane as well as high selectivities of $CH_4$ over $N_2$ which is of high interest for the purification of natural gas which is frequently diluted with $N_2$. The mechanically very stable, monolithic structure as well as the hierarchical mico-macroporosity suggests further applications, for example in monolithic chromatography. Furthermore, the successful synthesis of the PECONF materials in monolithic shape suggests that these materials can also be made as thin films for membrane applications.

Examples of Synthethis. Starting Materials: Hexachlorocyclotriphosphazene (PNC) of about 98% purity. 3,3'-Diaminobenzedine (DAB) of about 99% purity; Anhydrous dimethyl sulfoxide (DMSO) of about 99.8% purity. In a typical synthesis, about 1.5 mmol of DAB and 0.5 mmol of PNC were dissolved in 3, 7.5, 15 and 20 ml of DMSO for the synthesis of PECONF-1, PECONF-2, PECONF-3, and PECONF-4, respectively. The resulting solution was stirred for 30 minutes at RT. It was then heated at the temperature of 125° C. under stirring. Gelation started as early as 5 minutes. After 30 minutes, the sample cooled down to room temperature and the solid monoliths were collected. All the experiments were carried out in nitrogen atmosphere using Schlenk's apparatus. The DMSO from the as-synthesized monoliths was removed by soxhlet extraction using diethyl ether. The obtained solid monoliths were sonicated by in 30 ml of water, washed several times with water, and dried in vacuum at 100° C. The sonicator used in the present research was Cavitator Ultrasonic ME 11 (Mettler Electronics, USA) with a maximum power output of 200 W at 67 kHz.

Measurements: The microstructures of the specimens were studied by scanning electron microscopy (SEM) and transmission electron microscopy (TEM). The SEM images of the specimens were taken on a Hitachi S-4300 SEM. The TEM images were taken on a JEOL JEM-2000 electron microscope operated at 200 kV. X-ray diffraction was carried out using a Rigaku Rotaflex diffractometer with a Cu Kα radiation source (λ=0.15405 nm). The thermogravimetric analysis experiments were carried out both in air and nitrogen using a TA TGA 2950 instrument with a heating rate of 10° C. per minute. P and C CP MAS NMR spectra were obtained at 75.468 MHz on a General Electric NMR Instrument model GN-300 equipped with a Doty Scientific 7 mm MAS probe. C NMR chemical shifts were referenced to the downfield line of adamantine at 38.55 ppm, and for P NMR, the chemical shift of 85% $H_3PO_4$ was set to zero using external reference standards. The formation of the microporous framework structures were studied by nitrogen and carbon dioxide sorption using an Autosorb-1 instrument (Quantachrome, USA). Prior to analysis, all the samples were out-gassed overnight at 150° C. in vacuum.

Figure 2:
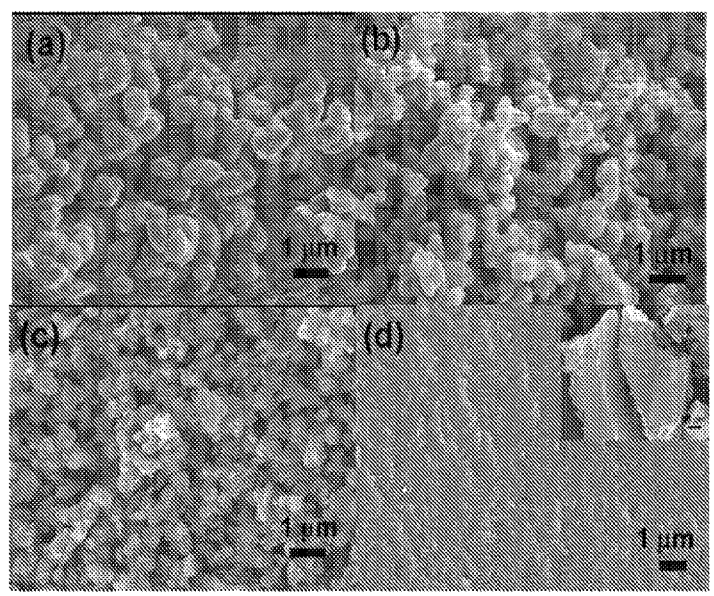
FIG. 2 illustrates a scanning electron microscope image of materials herein.
Figure 7A:
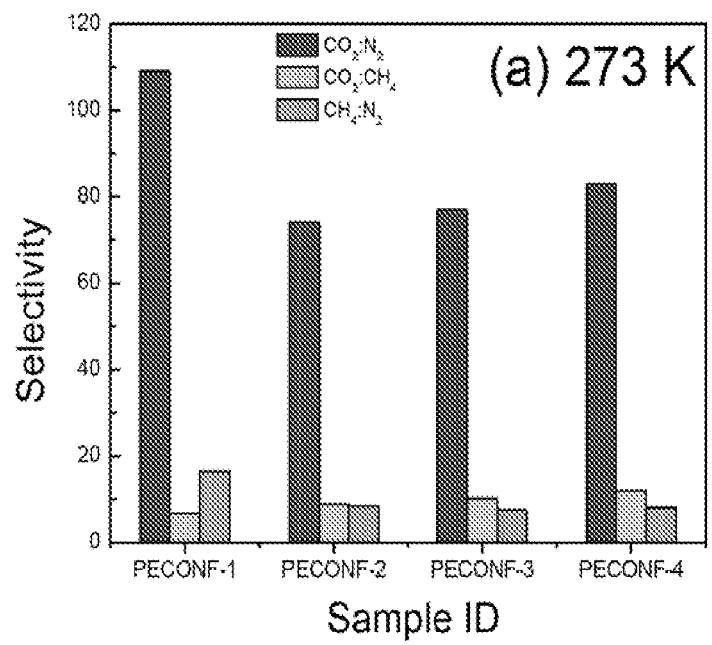
FIG. 7 graphically illustrates gas selectivity of sorption of PECONF materials herein.
Figure 7B:
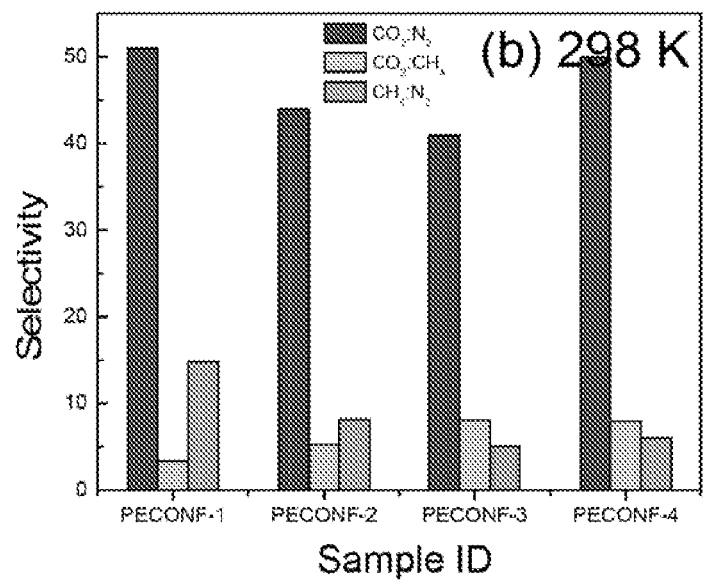
Figure 9:
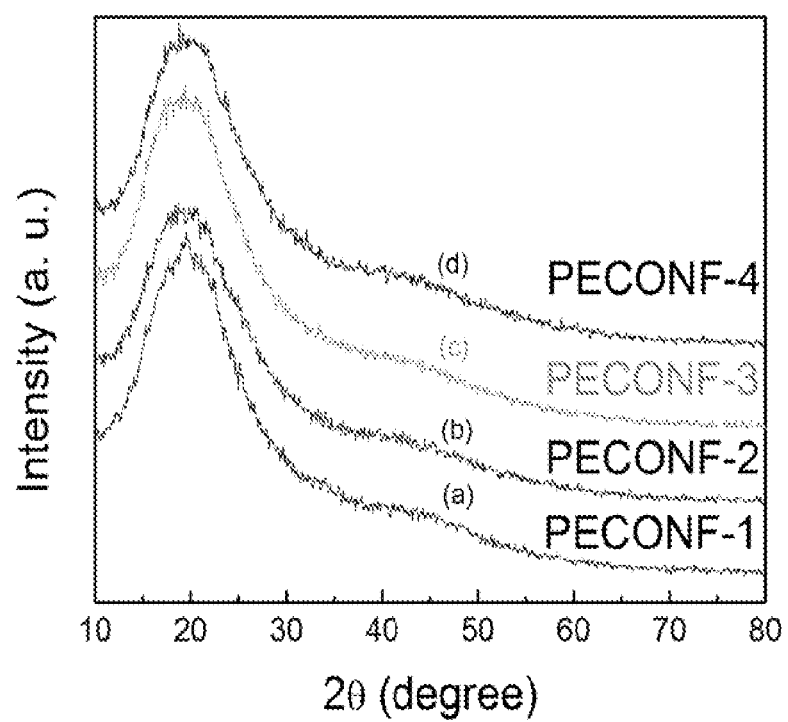
FIG. 9 illustrates XRD patterns Of PECONF materials herein.
Figure 14A:
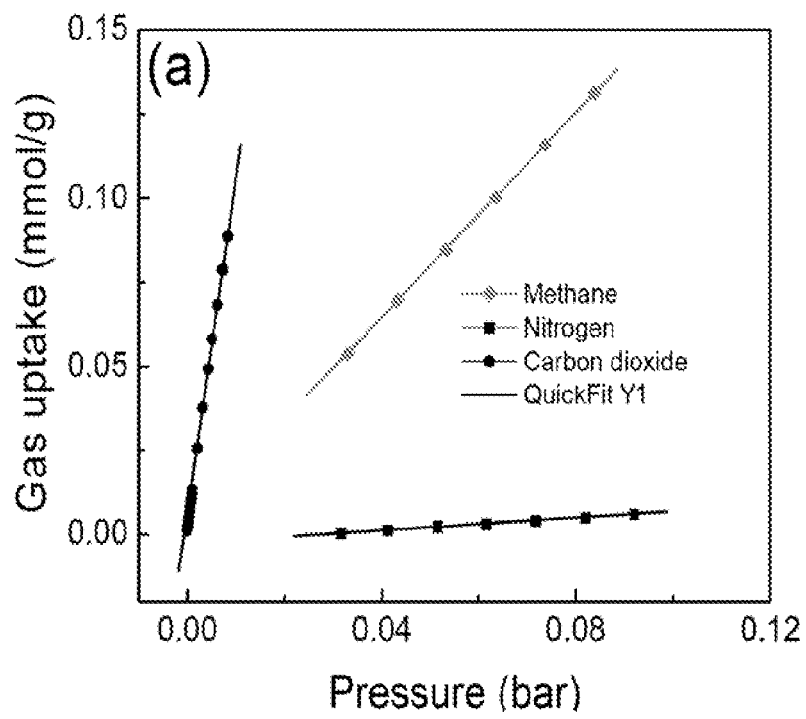
FIG. 14 illustrates the nitrogen, methane, and carbon dioxide sorption of PECONF-1 material herein.
Figure 14B:
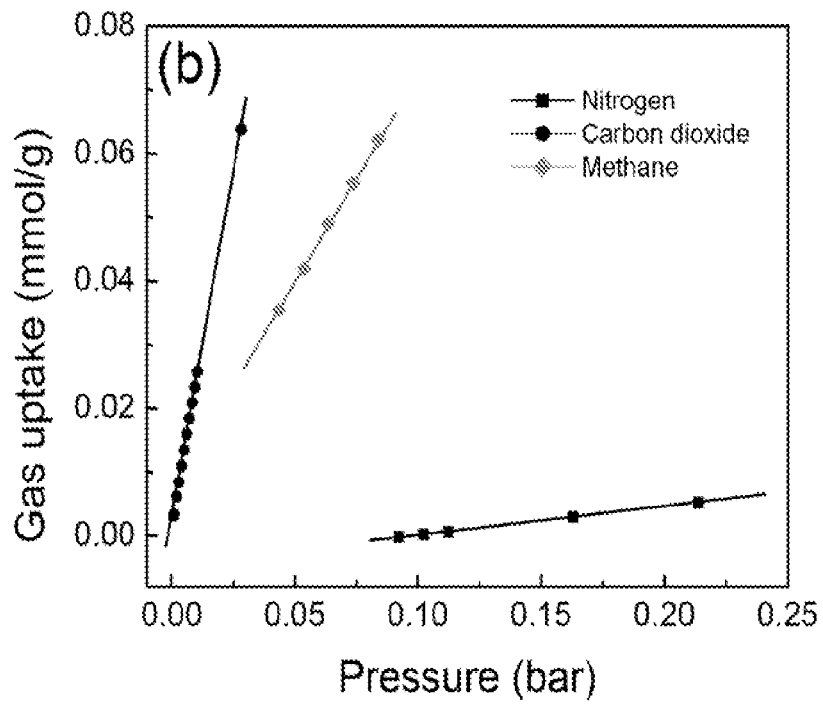
Figure 15A:
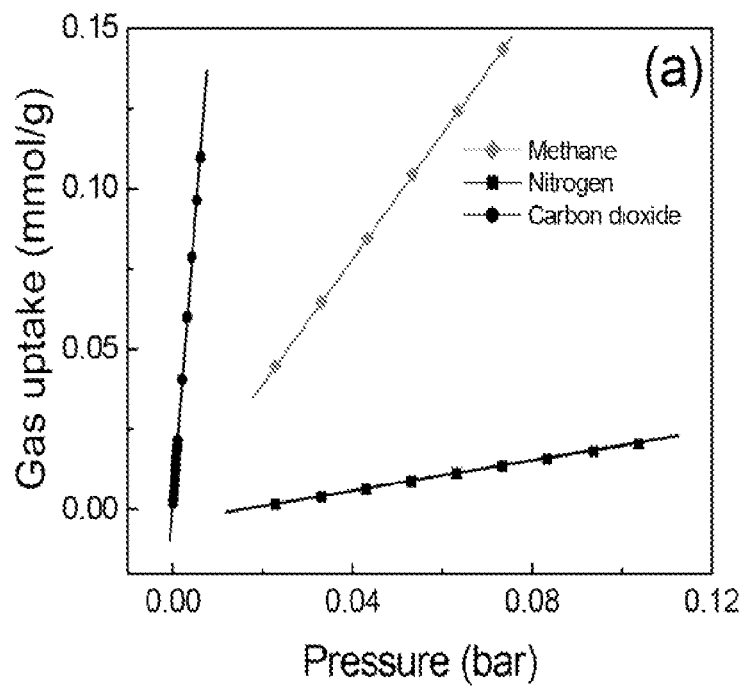
FIG. 15 illustrates the nitrogen, methane, and carbon dioxide sorption of PECONF-2 material herein.
Figure 15B:
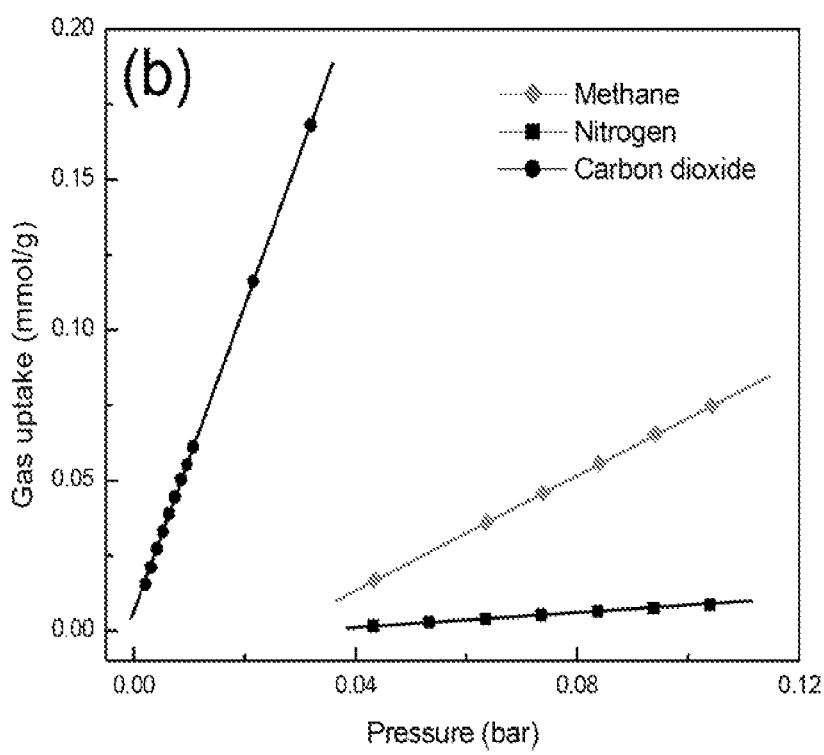

By way of further explanation, the figures attached represent properties and characteristics of the exemplary PECONF materials herein. FIG. 1 is an exemplary reaction scheme in accordance with the methods herein. FIG. 2 includes SEM images of (a) PECONF-1, (b) PECONF-2, (c) PECONF-3, and (d) PECONF-4. FIG. 3(a) illustrates $^{13}C$ CPMAS NMR spectra and 3(b) illustrates $^{31}P$ CPMAS NMR spectra of PECONF-1, PECONF-2, PECONF-3, and PECONF-4. FIG. 4 illustrates (a) $N_2$ and (b) $CO_2$ sorption of PECONFs measured at 77 K and 273 K, respectively, (c) $N_2$ and $CO_2$ sorption of PECONF-4 showing a very low $N_2$ uptake, and (d) pore size distribution of PECONF-1, PECONF-2, PECONF-3, and PECONF-4 calculated from the $CO_2$ isotherm measured at 273 K using the DFT method. FIG. 5 illustrates Isosteric heat of adsorption of PECONFs calculated from the $CO_2$ sorption data collected at 273 and 298 K. FIG. 6 illustrates (a) Methane sorption isotherms of PECONF-1, PECONF-2, PECONF-3, and PECONF-4 measured at 273 K, and (b) isosteric heat of adsorption of PECONFs calculated from the methane sorption data collected at 273 and 298 K. FIG. 7 illustrates selectivity of $CO_2:N_2$, $CO_2:CH_4$ and $CH_4:N_2$ for PECONFs at (a) 273 K and (b) 298 K, respectively. FIG. 8 illustrates TEM images of (a) PECONF-1, (b) PECONF-2, (c) PECONF-3, and (d) PECONF-4. FIG. 9 illustrates XRD patterns of (a) PECONF-1, (b) PECONF-2, (c) PECONF-3, and (d) PECONF-4. FIG. 10 illustrates FT-IR spectra of (a) PECONF-1, (b) PECONF-2, (c) PECONF-3, and (d) PECONF-4. FIG. 11 illustrates TGA and DTG thermograms of (a) PECONF-1, (b) PECONF-2, (c) PECONF-3, and (d) PECONF-4 measured in air with a heating rate of 10° C./min. FIG. 12 illustrates TGA and DTG thermograms of (a) PECONF-1, (b) PECONF-2, (c) PECONF-3, and (d) PECONF-4 measured in $N_2$ with a heating rate of 10° C./min. FIG. 13 illustrates methane sorption isotherm of PECONF-1, PECONF-2, PECONF-3, and PECONF-4 measured at 298 K. FIG. 14 illustrates the initial isotherm slopes for $N_2$, $CH_4$, and $CO_2$ of PECONF-1 at (a) 273 and (b) 298 K. FIG. 15 illustrates the initial isotherm slopes for $N_2$, $CH_4$, and $CO_2$ sorption of PECONF-2 at (a) 273 and (b) 298 K. FIG. 16 illustrates the initial isotherm slopes for $N_2$, $CH_4$, and $CO_2$ sorption of PECONF-3 at (a) 273 and (b) 298 K. FIG. 17 illustrates the initial isotherm slopes for $N_2$, $CH_4$, and $CO_2$ sorption of PECONF-4 at (a) 273 and (b) 298 K. FIG. 18 illustrates a Table (Table 1S) of PECONF characteristics, such as gas uptake, isosteric heat of adsorption and gas selectivities. The Table 1S of FIG. 18 is also reproduced below:

TABLE 1S

| Sample ID | $CO_2$ uptake (mmol·$g^{-1}$) at 1 atm | | Heat of adsorption for $CO_2$ | $CH_4$ uptake (mmol·$g^{-1}$) at 1 atm | | Heat of adsorption for $CH_4$ | Selectivity for $CO_2$ over $N_2$ | | Selectivity for $CO_2$ over $CH_4$ | | Selectivity for $CH_4$ over $N_2$ | |
|---|---|---|---|---|---|---|---|---|---|---|---|---|
| | 273K | 298K | kJ/mol | 273K | 298K | kJ/mol | 273K | 298K | 273K | 298K | 273K | 298K |
| PECONF-1 | 1.86 | 1.34 | 29 | 0.83 | 0.53 | 22.2 | 109:1 | 51:1 | 7:1 | 3:1 | 16:1 | 14:1 |
| PECONF-2 | 2.85 | 1.98 | 31 | 1.07 | 0.62 | 26.6 | 74:1 | 44:1 | 9:1 | 5:1 | 8:1 | 8:1 |
| PECONF-3 | 3.49 | 2.47 | 26 | 1.00 | 0.58 | 24.9 | 77:1 | 41:1 | 10:1 | 8:1 | 7:1 | 5:1 |
| PECONF-4 | 2.95 | 1.96 | 34 | 1.07 | 0.67 | 22.5 | 83:1 | 51:1 | 12:1 | 8:1 | 7:1 | 6:1 |

While this description is made with reference to exemplary embodiments, it will be understood by those skilled in the art that various changes may be made and equivalents may be substituted for elements thereof without departing from the scope. In addition, many modifications may be made to adapt a particular situation or material to the teachings hereof without departing from the essential scope. Also, in the description there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

The invention claimed is:

1. An organonitridic composition, wherein the composition comprises a plurality of cyclotriphosphazene units interconnected by diaminobenzidine units, and wherein the composition further comprises a porous framework.

2. The composition of claim 1, wherein the composition is amorphous.

3. The composition of claim 1, wherein the composition comprises micropores.

4. The composition of claim 3, wherein the composition further comprises macropores.

5. The composition of claim 1, wherein the composition selectively and reversibly adsorbs carbon dioxide ($CO_2$) from a fluid.

6. The composition of claim 1, wherein the composition is chemically stable in the presence of any one selected from the group consisting of water, oxygen gas, sulfur oxides, nitrogen gas, and nitrogenous oxides.

7. The composition of claim 1, wherein the composition is thermally stable up to at least about 400 degrees Celsius in a fluid environment.

8. The composition of claim 5, wherein the fluid comprises at least one selected from the group consisting of ambient air, a combustion exhaust stream, a natural gas stream, and an artificial gas stream.

9. The composition of claim 5, wherein the composition has a $CO_2$ adsorption capacity of up to at least about 3.5 mmol/g at standard temperature and pressure.

10. The composition of claim 9, wherein the composition exhibits a $CO_2:N_2$ gas adsorption selectivity up to about 109:1.

11. The composition of claim 9, wherein the adsorption capacity of the composition is reversed by changing at least one selected from the group consisting of temperature and pressure.

12. The composition of claim 5, wherein the adsorbed $CO_2$ binds to the composition with a binding energy that is greater than about 5 kJ/mol, and lower than about 50 kJ/mol.

13. The composition of claim 1, wherein the composition is thermally stable up to about 600 degrees Celsius in a nitrogen gas atmosphere.

14. The composition of claim 1, wherein the composition comprises the condensation product of a reaction comprising an organic solvent, a ditopic unit, and a tritopic unit.

15. The composition of claim 14, wherein the organic solvent is DMSO, the ditopic unit is a diaminobenzidine, and the tritopic unit is hexachlorocyclotriphosphazene.

16. The composition of claim 14, wherein the composition comprises a porosity and a surface area that are determined by the starting concentrations of the ditopic unit and the tritopic unit in the organic solvent.

17. The composition of claim 1, wherein the composition has a surface area ranging from about 100 to 850 m$^2$/g, and a pore volume ranging from about 0.3 cm$^3$ g$^{-1}$ to 0.7 cm$^3$ g$^{-1}$.

18. The composition of claim 1, wherein the composition has a monolithic structure, wherein the composition is at least one selected from the group consisting of a film and a membrane, and wherein the monolithic structure is mechanically stable to processes involving solvent exchange and solvent removal.

19. The composition of claim 1, wherein the composition has a methane ($CH_4$) adsorption capacity of up to at least about 1.07 mmol/g at standard temperature and pressure.

20. The composition of claim 1, wherein the composition selectively adsorbs $CH_4$ over $N_2$ with a ($CH_4:N_2$) selectivity ratio of at least 16:1.

21. An organonitridic composition, wherein the composition comprises a plurality of inorganic nitridic units interconnected by aromatic units, wherein the composition further comprises a porous framework, wherein the composition selectively and reversibly adsorbs $CO_2$ from a fluid, and wherein the composition has a $CO_2$ adsorption capacity of up to at least about 3.5 mmol/g at standard temperature and pressure.

22. The composition of claim 21, wherein the composition is amorphous.

23. The composition of claim 21, wherein the composition comprises micropores.

24. The composition of claim 23, wherein the composition further comprises macropores.

25. The composition of claim 21, wherein the composition is chemically stable in the presence of any one selected from the group consisting of water, oxygen gas, sulfur oxides, nitrogen gas, and nitrogenous oxides.

26. The composition of claim 21, wherein the composition is thermally stable up to at least about 400 degrees Celsius in a fluid environment.

27. The composition of claim 21, wherein the fluid comprises at least one selected from the group consisting of ambient air, a combustion exhaust stream, a natural gas stream, and an artificial gas stream.

28. The composition of claim 21, wherein the composition exhibits a $CO_2:N_2$ gas adsorption selectivity up to about 109:1.

29. The composition of claim 21, wherein the adsorption capacity of the composition is reversed by changing at least one selected from the group consisting of temperature and pressure.

30. The composition of claim 21, wherein the adsorbed $CO_2$ binds to the composition with a binding energy that is greater than about 5 kJ/mol, and lower than about 50 kJ/mol.

31. The composition of claim 21, wherein the composition is thermally stable up to about 600 degrees Celsius in a nitrogen gas atmosphere.

32. The composition of claim 21, wherein the composition comprises the condensation product of a reaction comprising an organic solvent, a ditopic unit, and a tritopic unit.

33. The composition of claim 32, wherein the organic solvent is DMSO, the ditopic unit is a diaminobenzidine, and the tritopic unit is hexachlorocyclotriphosphazene.

34. The composition of claim 33, wherein the composition comprises a porosity and a surface area that are determined by the starting concentrations of the ditopic unit and the tritopic unit in the organic solvent.

35. The composition of claim 21, wherein the composition has a surface area ranging from about 100 to 850 m$^2$/g, and a pore volume ranging from about 0.3 cm$^3$ g$^{-1}$ to 0.7 cm$^3$ g$^{-1}$.

36. The composition of claim 21, wherein the composition has a monolithic structure, wherein the composition is at least one selected from the group consisting of a film and a membrane, and wherein the monolithic structure is mechanically stable to processes involving solvent exchange and solvent removal.

37. An organonitridic composition, wherein the composition comprises a plurality of inorganic nitridic units interconnected by aromatic units, wherein the composition further comprises a porous framework, and wherein the composition has a methane adsorption capacity of up to at least about 1.07 mmol/g at standard temperature and pressure.

38. The composition of claim 37, wherein the composition selectively adsorbs $CH_4$ over $N_2$ with a ($CH_4:N_2$) selectivity ratio of at least 16:1.

* * * * *